(12) United States Patent
Lu et al.

(10) Patent No.: US 8,153,413 B2
(45) Date of Patent: Apr. 10, 2012

(54) HIGH ALKALINE PROTEASE AND USE THEREOF

(75) Inventors: Jie Lu, Yokosuka (JP); Zhi jun Li, Yokosuka (JP); Si Hung Vo, Yokosuka (JP); Yuji Hatada, Yokosuka (JP); Ken Takai, Yokosuka (JP); Susumu Ito, Yokosuka (JP); Koki Horikoshi, Yokosuka (JP)

(73) Assignee: Japan Agency for Marine-Earth Science and Technology, Yokosuka-shi (JP)

( * ) Notice: Subject to any disclaimer, the term of this patent is extended or adjusted under 35 U.S.C. 154(b) by 620 days.

(21) Appl. No.: 11/719,713

(22) PCT Filed: Nov. 16, 2005

(86) PCT No.: PCT/JP2005/021032
§ 371 (c)(1),
(2), (4) Date: Apr. 30, 2009

(87) PCT Pub. No.: WO2006/054595
PCT Pub. Date: May 26, 2006

(65) Prior Publication Data
US 2011/0045570 A1    Feb. 24, 2011

(30) Foreign Application Priority Data
Nov. 18, 2004   (JP) .................... 2004-334344

(51) Int. Cl.
| C12N 9/00 | (2006.01) |
| C12N 9/92 | (2006.01) |
| C12N 1/20 | (2006.01) |
| C12N 15/00 | (2006.01) |
| C07H 21/04 | (2006.01) |

(52) U.S. Cl. .................. 435/234; 435/183; 435/252.3; 435/320.1; 536/23.2

(58) Field of Classification Search .................. None
See application file for complete search history.

(56) References Cited

FOREIGN PATENT DOCUMENTS

| EP | 0 130 756 A1 | 1/1985 |
| JP | 5-211868 | 8/1993 |
| JP | 6-70765 | 3/1994 |
| JP | 9-121855 | 5/1997 |
| JP | 9-121856 | 5/1997 |
| JP | 2003-325186 | 11/2003 |
| JP | 2004-65171 | 3/2004 |
| JP | 2004-154003 | 6/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession BAD02409. Nov. 26, 2003.*
Accession QL6L29. Jul. 5, 2004.*
Ken Takai, et al., "*Alkaliphilus transvaalensis* gen. nov., sp. nov., an extremely alkaliphilic bacterium isolated from a deep South African gold mine", International Journal of Systematic and Evolutionary Microbiology, 2001, vol. 51, pp. 1245-1256.
Hiuga Saito, et al., "Preparation of Transforming Deoxyribonucleic Acid by Phenol Treatment", Biochim, Biophys. Acta, vol. 72, 1963, pp. 619-629.
Katsuhisa Saeki, et al., "Nucleotide and Deduced Amino Acid Sequences of a New Subtilisin from an Alkaliphilic *Bacillus* Isolate", Current Microbiology, vol. 47, 2003, pp. 337-340.
Oliver H. Lowry, et al., "Protein Measurement with the Folin Phenol Reagent", The Journal of Biological Chemistry,193, May 28, 1951, pp. 265-275.
Youhei Yamagata, et al., "Subtilisin sendai from alkalophilic *Bacillus* sp.: Molecular and enzymatic properties of the enzyme and molecular cloning and characterization of the gene, aprS", Enzyme and Microbial Technology, vol. 17, 1995, pp. 653-663.
Roland J. Siezen, et al., "Homology modelling and protein engineering strategy of subtilases, the family of subtilisin-like serine proteinases", Protein Engineering, vol. 4, No. 7, 1991, pp. 719-737.

* cited by examiner

*Primary Examiner* — Christian Fronda
(74) *Attorney, Agent, or Firm* — Oblon, Spivak, McClelland, Maier & Neustadt, L.L.P.

(57) ABSTRACT

The invention aims to provide a novel alkaline protease having peculiar properties such as high alkali activity, resistance to surfactants and calcium-dependent thermostability and exhibiting excellent performance in highly alkaline detergents, and a gene coding for the amino acid sequence thereof. There is provided an alkaline protease with such properties that an active pH range is from 5 to 13, an optimum pH is approximately 12.6, an optimum temperature is 70° C., no activity drop by heating is observed up to 65° C. at pH 10 and the optimum temperature and the thermostability are not affected by $Ca^{2+}$ ions. Specifically, there is provided, for example, an alkaline protease having an amino acid sequence constituting a mature enzyme as represented by SEQ ID NO: 3 or an amino acid sequence resulting from deletion, substitution, situs inversus arrangement, addition or insertion of a part of amino acids thereof, or derived from *Alkaliphillus transvaalensis*.
The protease cleaves 26 peptide bonds among 29 peptide bonds of acidic insulin B-chain.

34 Claims, 3 Drawing Sheets

HIGH ALKALINE PROTEASE AND USE THEREOF

Cross-Reference to Related Applications

The present application is a 35 U.S.C. §371 National Stage patent application of International patent application PCT/JP2005/021032, filed on Nov. 16, 2005, which claims priority to Japanese patent application JP 2004-334344, filed on Nov. 18, 2004.

TECHNICAL FIELD

The present invention relates to a novel alkaline protease having excellent activity under high alkaline conditions such as detergents, a gene coding for an amino acid sequence of the alkaline protease and a process for producing the alkaline protease.

BACKGROUND ART

A protease is a general term of an enzyme group that catalyzes hydrolysis of a peptide bond, and is widely distributed in microorganisms, animals and plants. Its application includes detergents for clothes, various detergents such as kitchen detergents, detergents for an automatic tableware washer and contact lens cleaners, toiletries such as bath products and keratolytics, food modifying agents for bread making, meat softening and marine product processing, digestion aids and antiinflammatory agents, and it has found wide acceptance in many fields.

It is a protease which is industrially mass-produced most among a large number of enzymes and has a great market scale. Among others, an alkaline protease for a detergent has played a significant role as an indispensable component in improvement of a washing power. As trade names of specifically marketed products as the alkaline protease, Sabinase, Cannase, Durazyme (manufactured by Novozyme), Makisakal (manufactured by Genencore), Blap (manufactured by Henkel) (all of them are registered trademarks), KAP (manufactured by Kao Corporation) are known.

These alkaline proteases for a detergent which have been used at present are derived from bacteria of the genus *Bacillus*, and belong to the subtilisin family classified in Class 1-S2 (refer to Non-patent Document 1). As true subtilisin, Subtilisin BPN' and Carlsberg belonging to Class 1-S1, and the like are well known.

With respect to the protease for a detergent, an enzyme for a detergent having more improved properties has been explored. Enzymes having stability to heat and surfactants (refer to, for example, Patent Document 1), enzymes acting on an insoluble protein such as keratin and having high specific activity (refer to, for example, Patent Document 2), enzymes having excellent activity in a low temperature region (refer to, for example, Patent Documents 3 and 4), a method for improving stability to oxidizers (refer to, for example, Patent Document 5) and the like have been reported.

However, many of these enzymes are problematic respectively in reactivity under quite high alkaline conditions, $Ca^{2+}$ ions-dependent thermostability, stability in concentrated surfactants or chelating agents and the like, and alkaline proteases so far discovered sometimes have not exhibited functions thereof satisfactorily.

Patent Document 1: Gazette of JP-A-6-70765
Patent Document 2: Gazette of JP-A-9-121855
Patent Document 3: Gazette of JP-A-5-211868
Patent Document 4: Gazette of JP-A-9-121856
Patent Document 5: Gazette of European Patent No. 0130756
Non-patent Document 1: Siezen et al., *Protein Eng.*, 4, 719-737,

DISCLOSURE OF THE INVENTION

Problems that the Invention is to Solve

The invention aims to provide a novel alkaline protease which is quite excellent in properties such as alkali resistance, resistance to surfactants and thermostability though having low homology to the foregoing ordinary subtilisin in amino acid sequence, and which has, for example, properties that expression of activity and thermostability are not influenced by $Ca^{++}$ ions, stability to surfactants is excellent and satisfactory performance is exhibited under high alkaline conditions, and a gene coding for the amino acid sequence thereof.

Means for Solving the Problems

For solving the foregoing problems, the present inventors have conducted investigations to find a protease which satisfactorily acts under a high alkaline region in nature. Consequently, they have found a novel alkaline protease which is excellent in stability to surfactants and has properties that are sufficiently exhibited even under high alkaline conditions from among enzymes produced by *Alkaliphillus transvaalensis* separated from ground water and a bottom mud of a circulating pool in a gold field of Transvaal District, South Africa, and have obtained a gene coding for the alkaline protease produced from this microorganism. As a result, the invention has been completed.

That is, the invention is to provide a novel alkaline protease having the following physicochemical properties.

(1) Action:
It acts on acidic insulin-B chain to cleave at least 20 peptide bonds and at most 26 peptide bonds among 29 peptide bonds thereof.

(2) Substrate Specificity:
It catalyzes hydrolysis of casein, elastin, keratin and hemoglobin which are natural proteins. It catalyzes hydrolysis of N-succinyl-Ala-Ala-Pro-Phe-p-nitroanilide ("Ala-Ala-Pro-Phe" disclosed as SEQ ID NO: 8), N-glutaryl-Ala-Ala-Pro-Leu-p-nitroanilide ("Ala-Ala-Pro-Leu" disclosed as SEQ ID NO: 9), N-succinyl-Ala-Ala-Pro-Met-p-nitroanilide ("Ala-Ala-Pro-Met" disclosed as SEQ ID NO: 10), N-methoxysuccinyl-Ala-Ile-Pro-Met-p-nitroanilide ("Ala-Ile-Pro- Met" disclosed as SEQ ID NO: 11) and N-succinyl-Ala-Ala-Val-Ala-p-nitroanilide ("Ala-Ala- Val-Ala" disclosed as SEQ ID NO: 12) which are synthetic substrates to form p-nitroaniline.

(3) Active pH and Optimum pH:
An active pH range is from 5 to 13, a stable pH range is from 5 to 11 (treatment at 50° C. for 10 minutes), and an optimum pH is approximately 12.6.

(4) Optimum Temperature and Thermostability:
An optimum temperature is 70° C., and it is stable up to 65° C. without activity drop by heating (at pH 10 for 10 minutes). The optimum temperature and the thermostability are still unchanged in the presence of $Ca^{2+}$ ions.

(5) Influence of Surfactants
Activity is not inhibited by linear sodium alkylbenzene sulfonate, sodium polyoxyethylene alkyl sulfate, sodium dodecyl sulfate, sodium α-olefin sulfonate, sodium alkane sulfonate, α-sulfo-fatty acid ester and polyoxyethylene alkyl alcohol (trade name: Softanol 70H).

(6) Molecular Weight:

A molecular weight measured by sodium dodecyl sulfate-polyacrylamide gel electrophoresis is from 31,000 to 32,000.

Further, the invention is to provide the novel alkaline protease which has an amino acid sequence represented by SEQ ID NO: 3 of Sequence Listing, an amino acid sequence resulting from deletion, substitution, situs inversus arrangement, addition or insertion of one or plural amino acids in the foregoing amino acid sequence, or an amino acid sequence having at least 65% homology to the amino acid sequence represented by SEQ ID NO: 3 of Sequence Listing.

Still further, the invention is to provide the novel alkaline protease which is derived from *Alkaliphillus transvaalensis*.

Furthermore, the invention is to provide a novel alkaline protease precursor having an amino acid sequence represented by SEQ ID NO: 2 of Sequence Listing or an amino acid sequence resulting from deletion, substitution, situs inversus arrangement, addition or insertion of one or plural amino acids in the foregoing amino acid sequence.

Furthermore, the invention is to provide a polynucleotide which is a gene coding for the amino acid sequence of the novel alkaline protease or its precursor, and which is selected from the group consisting of the following (a) to (f), (a) a polynucleotide coding for a polypeptide having an amino acid sequence constituting a mature enzyme as represented by SEQ ID NO: 3, (b) a polynucleotide coding for a polypeptide having an amino acid sequence resulting from deletion, substitution, situs inversus arrangement, addition or insertion of one or plural amino acids in the amino acid sequence constituting the mature enzyme as represented by SEQ ID NO: 3, (c) a polynucleotide coding for a polypeptide having an amino acid sequence represented by SEQ ID NO: 2, (d) a polynucleotide coding for a polypeptide having an amino acid sequence resulting from deletion, substitution, situs inversus arrangement, addition or insertion of one or plural amino acids in the amino acid sequence represented by SEQ ID NO: 2, (e) a polynucleotide having a nucleotide sequence represented by SEQ ID NO: 1, and (f) a polynucleotide coding for a protein, which is hybridized with the polynucleotide comprising the nucleotide sequence represented by SEQ ID NO: 1 under stringent conditions and which has alkaline protease activity.

Furthermore, the invention is to provide a recombinant vector having the polynucleotide and a microorganism which is transformed with the recombinant vector.

Furthermore, the invention is to provide a process for producing the alkaline protease having the physicochemical properties or the amino acid sequence, which comprises culturing *Alkaliphillus transvaalensis* or the transformed microorganism, and collecting the alkaline protease from the culture solution.

Advantage of the Invention

The novel high alkaline protease of the invention is, in comparison with ordinary alkaline proteases, an alkaline protease in which expression of activity and thermostability are not influenced by $Ca^{2+}$ ions, excellent alkali resistance and excellent resistance to surfactants are provided and quite excellent performance is exhibited even under high alkalinity with pH of 12 or more. Accordingly, it can be utilized in detergents, many other products and application fields using action of enzymes under neutral to high alkaline conditions.

BEST MODE FOR CARRYING OUT THE INVENTION

The novel high alkaline protease of the invention (hereinafter sometimes referred to as the "invention enzyme") has, in comparison with ordinary alkaline proteases, good activity in a high alkaline region and excellent resistance to surfactants. The invention enzyme has the following properties.

1) Action

It catalyzes hydrolysis of proteins. It has peculiar properties that when acidic insulin B-chain is used as a substrate, it cleaves all peptide bonds except Phe-Val bond on the N-terminal side and Thr-Pro-Lys bond on the C-terminal side. Regarding the cleavage of the acidic insulin B-chain, it cleaves Leu-Tyr bond at the initial stage and finally at least 20 bonds and at most 26 bonds except Phe-Val bond on the N-terminal side and Thr-Pro-Lys bond on the C-terminal side.

It has been known that ordinary proteases cleave a part of peptide bonds of the acidic insulin B-chain. However, it has been entirely unknown that many bonds are cleaved as noted above.

2) Substrate Specificity:

It catalyzes hydrolysis of casein, elastin and keratin which are natural proteins, and has high activity to hemoglobin as a blood component. When hydrolytic activity to casein is defined as 100%, that to hemoglobin is approximately 73%, that to keratin approximately 22% and that to elastin approximately 13%.

Further, the invention enzyme has high activity to N-succinyl-Ala-Ala-Pro-Phe-p- nitroanilide (hereinafter sometimes abbreviated as "AAPF" (SEQ ID NO: 8)), N-glutaryl-Ala-Ala- Pro-Leu-p-nitroanilide (hereinafter sometimes abbreviated as "AAPL" (SEQ ID NO: 9)), N- succinyl-Ala-Ala-Pro-Met-p-nitroanilide (hereinafter sometimes abbreviated as "AAPM" (SEQ ID NO: 10)), N-methoxysuccinyl-Ala-Ile-Pro-Met-p-nitroanilide (hereinafter sometimes abbreviated as "AIPM" (SEQ ID NO: 11)) and N-succinyl-Ala-Ala-Val-Ala-p-nitroanilide (hereinafter sometimes abbreviated as "AAVA" (SEQ ID NO: 12)) as synthetic substrates and catalyzes hydrolysis thereof to form p-nitroaniline.

Moreover, it has also activity to other substrates such as N-succinyl-Ala-Ala-Ala-p- nitroanilide (hereinafter sometimes abbreviated as "AAA"), N-succinyl-Ala-Ala-p-nitroanilide (hereinafter sometimes abbreviated as "AA"), N-p-tocyl-Gly-Pro-Lys-p-nitroanilide (hereinafter sometimes abbreviated as "To-GPK"), N-succinyl-Gly-Gly-Phe-p-nitroanilide (hereinafter sometimes abbreviated as "GGF"), N-carbobenzoxy-Phe-Val-Arg-p-nitroanilide (hereinafter sometimes abbreviated as "Z-FVR"), butyroxycarbonyl-Leu-Ser-Thr-Arg-p-nitroanilide (hereinafter sometimes abbreviated as "LSTR" (SEQ ID NO: 13)), N-carbobenzoxy-Pro-citrulline- p-nitroanilide (hereinafter sometimes abbreviated as "CBZ-Pro-Cit"), though the activity is lower than the foregoing activity.

3) Active pH and Optimum pH:

An active pH range is from 5 to 13, a stable pH range is from 5 to 11 (treatment at 50° C. for 10 minutes), and an optimum pH is approximately 12.6. Even when pH exceeds 12, a tendency of a decrease in enzymatic activity is not observed.

4) Optimum Temperature and Thermostability:

An optimum active temperature is 70° C., and it is stable up to 65° C. without activity drop by heating (at pH 10 for 10 minutes). The optimum temperature and the thermostability are unchanged regardless of the presence or absence of $Ca^{2+}$ ions. In various ordinary proteases, it is known that the optimum temperature is generally increased by 10 to 20° C. and thermostability is also increased in the presence of $Ca^{2+}$ ions. However, such phenomena are not observed at all in the invention enzyme, and it has peculiar properties different from the ordinary ones.

5) Influence of Metal Ions

At a concentration of 1 mM, it is not inhibited by $Li^+$, $K^+$, $Na^+$, $Ba^{2+}$, $Ca^{2+}$, $Cd^{2+}$, $Cu^{2+}$, $Co^{2+}$, $Mg^{2+}$, $Ni^{2+}$, $Fe^{2+}$, $Fe^{3+}$, $Sn^{2+}$, $Mn^{2+}$, $Pb^{2+}$ and $Zn^{2+}$. At a concentration of 1 mM, it is inhibited by $Hg^{2+}$ only.

6) Influence of Surfactants:

Activity is not inhibited by linear sodium alkylbenzene sulfonate (SAS), sodium polyoxyethylene alkyl sulfate (ES), sodium dodecyl sulfate (SDS), sodium α-olefin sulfonate (AOS), sodium alkane sulfonate (AS), α-sulfo-fatty acid ester (α-SFE) and polyoxyethylene alkyl alcohol (trade name: Softanol 70H).

7) Inhibitor:

It is not inhibited by EDTA (ethylenediamine tetraacetic acid) as a chelating agent at a high concentration of 100 mM. It is little inhibited even in the presence of p-chloromercuribenzoic acid (1 mM), urea (0.5 M), SDS (1 mM) and triton X-100 (1%). It is inhibited by PMSF (phenylmethanesulfonyl fluoride) (1 mM) and chymostatin (30 ppm) as a serine protease inhibitor.

8) Molecular Weight:

A molecular weight measured by sodium dodecyl sulfate-polyacrylamide gel electrophoresis is from 31,000 to 32,000.

Such a high alkaline protease of the invention is obtained by the following method, which is not particularly limitative though. For example, it is found from among enzymes produced by *Alkaliphillus transvaalensis*. As an example of microorganisms belonging to the genus *Alkaliphillus*, there is *Alkaliphillus transvaalensis* SAGM1 strain which is an absolute anaerobic alkalophilic bacterium separated from ground water or a bottom mud of a circulating pool (temperature: 34.2° C., pH: 11.63) present at a depth of 3,200 m in a gold field at Transvaal District, South Africa and which is a heterotrophic bacterium with a composite organic substrate (yeast extract and trypton) as energy and carbon source. This microorganism is deposited in American Type Culture Collection, USA (ATCC, residence: 10801 University Blvd. Manassas, Va. 20110-2209, USA) as ATCC 700919 and in Rikagaku Kenkyusho, Biseibutsukeito Hozon Shisetsu, Japan (JCM, residence: 2-1 Hirosawa, Wako, Saitama 351-0198) as JCM 10712, and it can be procured from these depositories. This microorganism has the following bacteriological properties.

Bacteriological Properties of *Alkaliphillus transvaalensis* SAGM1:

A. Morphological Properties
  (a) Cell morphology: straight or curved rod
  (b) Cell size: (0.4 to 0.7 μm)×(3 to 6 μm)
  (c) Mobility: not observed
  (d) Spore: observed (diameter 0.8 to 1.0 μm)
  (e) Gram staining: positive B. Growth State in Various Media
  (a) Growth state in a composite substrate standard agar medium: A circular, low-convex colony with a whole smooth edge is formed. The surface of the colony is cream-colored without gloss.
  (b) Composite substrate standard liquid culture: turbid
  (c) Autotrophic medium: not grown C. Physiological Properties
  (a) Reduction of nitrate: negative
  (b) Reduction of thiosulfuric acid: positive
  (c) Reduction of elemental sulfur: positive
  (d) Formation of hydrogen sulfide: positive
  (e) Reduction of fumaric acid: positive
  (f) Formation of hydrogen by fermentation: positive
  (g) Inhibition of fermentation with molecular hydrogen: positive
  (h) Use of starch: negative
  (i) Use of monosaccharides and oligosaccharides: negative
  (j) Use of organic acids: positive
  (k) Use of lower alcohols: positive
  (l) Use of casein: positive
  (m) Growth temperature range: growable at 20 to 50° C.
  (n) pH range of growth: well grown at pH 8.5 to 12.4
  (o) Aerobic culture: ungrowable under aerobic condition This *Alkaliphillus transvaalensis* was accumulated by, for example, inoculating the bottom mud sample in a standard medium obtained by adding a composite organic substrate containing a yeast extract and trypton as energy and carbon source and thiosulfuric acid as an electron acceptor to a basic salt medium of a chemical composition similar to that of ground water and rendering the medium alkaline with sodium carbonate and potassium hydroxide and culturing the sample at 37° C. for 3 days under anaerobic conditions of 80% nitrogen and 20% carbon dioxide. Then, this microorganism was isolated by a limiting diluting method, and various properties thereof were determined.

The bacteriological properties of *Alkaliphillus transvaalensis* have been described in detail in the report of Takai Ken, one of the present inventors, et al. (*Int. J. Syst. Evol. Microbiol.* 51, 1245-1256, 2001), and the description thereof is here quoted in the present specification. This microorganism can be grown under the highest alkaline conditions among alkalophilic bacteria which have been known at present.

In order to obtain the invention enzyme using the foregoing microorganism, it is advisable, for example, that the strain is inoculated in the medium and cultured in a usual manner according to the handling of anaerobic bacteria, after which the invention enzyme is recovered from the culture.

It is desirable that appropriate amounts of assimilable carbon and nitrogen sources are incorporated in a medium used in culturing. The carbon and nitrogen sources are not particularly limited. Examples of the carbon source include glucose, galactose, fructose, sucrose, maltose, raffinose, trehalose, glycerol, melibiose, assimilable organic acids such as citric acid, and the like. As the nitrogen source, organic nitrogen sources, for example, corn gluten meal, soybean powder, corn steep liquor, casamino acid, yeast extract, fermamedia, meat extract, trypton, soyton, polypeptone, soybean meal, cotton seed oil cake and cultivator are effective. Various inorganic salts are essential, and it is advisable that artificial brine is added to a medium at a rate of 1/10.

The culturing temperature is from 20 to 50° C., especially preferably 40° C., and pH is from 8.5 to 12.4, especially preferably from 10.0 to 11.0. Under these conditions, the culturing is completed usually in from 1 to 3 days.

The invention enzyme is accumulated in a culture supernatant, and a residual culture solution obtained by separating cells may be used as a crude enzyme solution. Further, the crude enzymes can be purified by an ordinary purification method such as ion exchange chromatography or gel filtration chromatography. These may be recovered, as required, by a method such as ultrafiltration or precipitation, and used by granulation via an appropriate method.

More specifically, the crude enzyme solution may be used, for example, by being further separated and purified via a combination of known methods such as a salting-out method, a precipitation method and an ultrafiltration method, for example, ion exchange chromatography, isoelectric chromatography, hydrophobic chromatography, gel filtration chromatography, adsorption chromatography, affinity chromatography and reversed phase chromatography, as required.

As another method for obtaining the invention enzyme, there is a method in which a gene coding for the amino acid sequence of the invention enzyme is obtained from the foregoing strain, a recombinant microorganism is then prepared by a genetic engineering technique and this recombinant microorganism is cultured. Specifically, it is possible that the nucleotide sequence coding for the amino acid sequence of the invention enzyme is obtained from the foregoing strain, this nucleotide sequence is then incorporated into an appropriate vector, a host such as E. coli is transformed with this vector, the transformant is cultured to produce the invention enzyme and the invention enzyme is collected from the culture. A process for producing the invention enzyme by a specific gene engineering technique is described below.

The gene of the alkaline protease has generally a long prepro sequence. The pre sequence is necessary for extracellular secretion of the enzyme, and the pro sequence is a necessary sequence for forming an active stereostructure of the enzyme. The present inventors have found an entire gene sequence coding for an alkaline protease precursor having a prepro sequence represented by SEQ ID NO: 1 of Sequence Listing and an amino acid sequence of the precursor represented by SEQ ID NO: 2. They have further found an amino acid sequence of a high alkaline protease, namely an amino acid sequence of a mature enzyme, of the invention which is extracellularly produced, the amino acid sequence being represented by SEQ ID NO: 3.

The invention enzyme is a polypeptide having an amino acid sequence constituting a mature enzyme as represented by SEQ ID NO: 3, an amino acid sequence resulting from deletion, substitution, situs inversus arrangement, addition or insertion of one or plural amino acids in the foregoing amino acid sequence or an amino acid sequence having at least 65% homology to the foregoing amino acid sequence, preferably a polypeptide having an amino acid sequence constituting a mature enzyme as represented by SEQ ID NO: 3 or an amino acid sequence resulting from deletion, substitution, situs inversus arrangement, addition or insertion of one or plural amino acids in the foregoing amino acid sequence. Accordingly, the gene coding for the amino acid sequence of the high alkaline protease in the invention is a nucleotide sequence corresponding to this.

Moreover, the precursor of the invention enzyme is an amino acid sequence represented by SEQ ID NO: 2 or an amino acid sequence resulting from deletion, substitution, situs inversus arrangement, addition or insertion of one or plural amino acids in the foregoing amino acid sequence. Accordingly, the gene including the gene coding for the amino acid sequence of the high alkaline protease in the invention is a nucleotide sequence corresponding to this.

As the gene coding for the amino acid sequence of the invention enzyme or its precursor, a polynucleotide selected from the group consisting of the following (a) to (f) is specifically mentioned.

(a) a polynucleotide coding for a polypeptide having an amino acid sequence constituting a mature enzyme as represented by SEQ ID NO: 3, (b) a polynucleotide coding for a polypeptide having an amino acid sequence resulting from deletion, substitution, situs inversus arrangement, addition or insertion of one or plural amino acids in the amino acid sequence constituting the mature enzyme as represented by SEQ ID NO: 3, (c) a polynucleotide coding for a polypeptide having an amino acid sequence represented by SEQ ID NO: 2, (d) a polynucleotide coding for a polypeptide having an amino acid sequence resulting from deletion, substitution, situs inversus arrangement, addition or insertion of one or plural amino acids in the amino acid sequence represented by SEQ ID NO: 2, (e) a polynucleotide having a nucleotide sequence represented by SEQ ID NO: 1, and (f) a polynucleotide coding for a protein, which is hybridized with the polynucleotide comprising the nucleotide sequence represented by SEQ ID NO: 1 under stringent conditions and which has alkaline protease activity.

An amino acid sequence resulting from deletion, substitution, situs inversus arrangement, addition or insertion of one or plural amino acids as described herein means a sequence equivalent to the original sequence, and it is an amino acid sequence resulting from deletion, substitution, situs inversus arrangement, addition or insertion of one or plural amino acids, preferably one to ten amino acids, and this sequence still keeps alkaline protease activity. The addition includes addition of one or plural amino acids to both ends. As this amino acid sequence, a sequence having at least 65% homology, preferably at least 75% homology is mentioned.

The "stringent conditions" as described herein include conditions described in "Molecular Cloning: A Laboratory Manual 2nd ed." (edited by T. Maniatis et al., published by Cold Spring Harbor Laboratories, 1989) and the like. Specifically, the stringent conditions are, for example, conditions that a substance is stored along with a probe overnight at a temperature of from 50 to 65° C. in a solution comprising 6×SSC (1×SSC composition: 0.15 M NaCl and 0.015 M sodium citrate, pH 7.0), 0.5% SDS, 5×Denhart and 100 µg/ml thermally denatured herring sperm DNA for Hybridization.

The base sequence coding for the equivalent amino acid sequence can be prepared by a known method such as a site-specific mutation inducing method. For example, it is advisable to introduce mutation by a kit for introducing mutation (Mutan-super Express Km Kit: manufactured by Takara) using a site-specific mutation inducing method.

When the amino acid sequence of the high alkaline protease represented by SEQ ID NO: 3 of Sequence Listing in the invention is compared with the amino acid sequence of the known alkaline protease in homology, its homology to Alkaline Protease LD1 (Saeki et al., Curr. Microbiol. 47, 337-340, 2003) produced by Bacillus sp. KSM-LD1 strain is 64.0%, and its homology to Subtilisin Sendai (Yamagata et al., Enzyme Microb. Technol. 17,653-663, 1995) produced by Bacillus sp. G-825-6 strain is 61.0%. Its homology to other known alkali proteases is only 60% or less. This indicates that the alkaline protease coded for by the high alkaline protease gene of the invention is a novel enzyme. Accordingly, the alkaline protease having at least 65% homology to the amino acid sequence of SEQ ID NO: 3 and the gene coding for this are included in the invention.

Incidentally, the search for homologous enzymes was conducted using BLASTP of National Center for Biotechnology Information (NCBI) (http://www.ncbi.nlm.nih.gov/BLAST/), and the values of the homology were obtained by a Peptide search homology program of GENETYX-MAC (version 10.1; manufactured by Software).

A recombinant microorganism productive of the invention enzyme can be prepared by a combination of known steps. That is, formation of the nucleotide sequence coding for the invention enzyme from Alkaliphillus transvaalensis, its amplification, insertion of the nucleotide sequence into the vector, transformation of a host with the gene and the like are properly conducted using methods described in the documents in the fields thereof.

Of these, as an example of a method for preparing a recombinant microorganism, the following method can be used, though it is not critical in particular. That is, the high alkaline protease gene of the invention is obtained from *Alkaliphillus transvaalensis* by shotgun cloning, PCR amplification with a specific primer or the like. This gene is introduced into Gram-negative bacteria typified by EK-type *Escherichia coli* and the like or Gram-positive bacteria typified by BS-type *Bacillus subtilis* and the like to obtain a recombinant microorganism. In the transformation, an extranuclear gene such as a plasmid is used as a vector, or a method using a DNA incorporation ability inherent in host bacteria or the like is available.

Culturing of the above-formed recombinant microorganism, obtainment of the invention enzyme from the culture and purification of the enzyme can also be conducted by the foregoing methods, known methods or methods similar thereto.

In the invention, the activity of the invention enzyme can be measured by a casein method or a synthetic substrate method to be described later.

The invention is illustrated more specifically below by referring to Examples. In Examples, "%" is % by mass, unless otherwise instructed.

EXAMPLE 1

(i) Incubation of Alkaline Protease-Productive Bacteria

*Alkaliphillus transvaalensis* of Deposit No. JCM 10712 procured from Rikagaku Kenkyusho Biseibutsukeito Hozon Shisetsu (JCM) was incubated at 40° C. for 24 hours according to the method described in the Takai et al. report (*Int. J. Syst. Evol. Microbiol.*, 51, 1245-1256, 2001) under inclusion of 1.5 atm nitrogen gas using media (pH 10.5) shown in Tables 1 and 2 below. When protease activity was high, the culture solution was centrifuged (10,000×g, 20 minutes).

TABLE 1

Composition of medium for production of protease

| Components | Composition |
|---|---|
| Sodium chloride | 0.3% |
| Potassium hydrogenphosphate | 0.0014% |
| Calcium chloride | 0.0014% |
| Ammonium chloride | 0.00125% |
| Sodium nitrate | 0.00125% |
| Magnesium sulfate | 0.034% |
| Magnesium chloride | 0.0418% |
| Potassium chloride | 0.0033% |
| Nickel chloride | 0.000005% |
| Sodium selenite | 0.000005% |
| Iron (III) citrate | 0.04% |
| Sodium sulfate | 0.1% |
| Sodium fumarate | 0.32% |
| Sodium carbonate | 4.0% |
| Sodium hydroxide | 0.02% |
| Yeast extract (Difco) | 0.2% |
| Trypton (BBL) | 0.2% |
| Sodium citrate | 0.1% |
| Sodium succinate | 0.1% |
| Microelement solution | 1.0% |

TABLE 2

Composition of microelement solution

| Components | Composition |
|---|---|
| Nitrilotriacetic acid | 0.15% |
| Manganese sulfate | 0.05% |
| Cobalt sulfate | 0.05% |
| Zinc sulfate | 0.018% |
| Copper sulfate | 0.001% |
| Potassium alm | 0.002% |
| Boric acid | 0.001% |
| Sodium molybdate | 0.001% |

(ii) Purification of a Protease

The resulting culture supernatant was dialyzed overnight against city water of 4° C. using a dialysis membrane. A dialysis inner solution was adjusted to pH 7 by addition of 1 M phosphate buffer, and then applied to DEAE-Toyopearl (manufactured by Tosoh Corp.) equilibrated with 10 mM phosphate buffer (pH 7.0) to recover a non-absorptive protease active fraction. Further, the active fraction was applied to CM-Toyopearl (manufactured by Tosho Corp.) equilibrated with the same buffer to recover a non-adsorptive protease active fraction. This active fraction was analyzed by the SDS-electrophoresis method, and it was confirmed that the protease was obtained as a nearly uniform protein. Incidentally, the protein concentration was measured by the Lowry et al. method (*J. Biol. Chem.*, 193, 265-275, 1981) using bovine serum albumin (manufactured by Biorad) as a standard protein.

(iii) Determination of an Amino Acid Sequence of an Alkaline Protease Derived from *Alkaliphillus transvaalensis*

The purified alkaline protease (hereinafter referred to as "alkaline protease ALTP") obtained in (ii) was blotted on a PVDF membrane (manufactured by Biorad), and an amino acid sequence from an amino terminal was determined with an amino acid sequencer (476A type, manufactured by Applied Biosystems). Consequently, the amino acid sequence from the amino terminal of alkaline protease ALTP obtained herein was Ala-Gln-Ser-Thr-Pro-Trp-Gly-Val-Thr-Arg (SEQ ID NO: 14). Further, the purified enzyme was partially digested with trypsin, and the amino acid sequence from the amino terminal of one of the resulting peptide fragments was determined to be Met-Ala-Ala-Pro-His-Val-Ala-Gly-Val (SEQ ID NO: 15).

(iv) Cloning of a Gene and Determination of a Base Sequence

Primer 1 (5'-GCNCARWSNACNCCNTGGGG-3' wherein N represents A, T, G or C; R represents A or G; W represents T or A; and S represents G or C) represented by SEQ ID NO: 4 was synthesized on the basis of the amino acid sequence from the amino terminal of alkaline protease ALTP obtained in (iii). Meanwhile, amino acid sequences of enzymes belonging to the serine protease family derived from procaryotes were compared. As a result, Gly-His-Gly-Thr-His- Val-Ala-Gly (SEQ ID NO: 16) was found as a common amino acid sequence of these enzymes, and primer 2 (5'-CCNGCNACRTGNGTNCCRTG-3') represented by SEQ ID NO:5 as presumed from the amino acid sequence having high preservability was synthesized. A chromosomal DNA was prepared from Alkaliphillus transvaalensis according to the method of Saito and Miura (Biocheim. Biophys. Acta, 72, 619-629, 1963). PCR amplification was conducted using this chromosome as a temperate, the foregoing primers 1 and 2 and LA Taq DNA polymerase (manufactured by Takara Bio). The PCR conditions were that after denaturation at 94° C. for 1 minute, a cycle of 94° C. for 30 seconds, 50° C. for 30 seconds and 72° C. for 30 seconds was repeated 30 times. Consequently, a DNA fragment of approximately 0.2 kb was amplified, and a sequence of the amplified DNA fragment was determined using Big Dye Terminator Cycle Sequencing Kit (manufactured by Applied Biosystems). Further, gene sequences in the upstream and downstream regions were determined using a primer synthesized on the basis of the determined base sequence and LA PCR in vitro gene cloning kit (manufactured by Takara Bio). As a result, a base sequence of an open reading frame of a serine protease gene comprising 1,131 base pairs as represented by SEQ ID NO: 1 and an amino acid sequence comprising 376 amino acids as represented by SEQ ID NO: 2 were determined. Moreover, an amino acid sequence of a mature enzyme of the high alkaline protease of the invention as represented by SEQ ID NO: 3 was determined. The amino terminal amino acid sequence of the purified enzyme and the amino terminal amino acid sequence of the peptide fragment obtained by partial digestion of the purified enzyme with trypsin were confirmed from the determined sequences.

(v) Production of Alkaline Protease ALTP with *Bacillus subtilis* Transformant

PCR amplification was conducted on the basis of the gene coding for alkaline protease ALTP determined in (iv) with primer 3 (5'-CATTTTTACACCAATATTTACATTT-TAATTCCAAG-3') represented by SEQ ID NO: 6 of Sequence Listing and primer 4 (5'-ATTTCCAGCTATT-TATCTCCTTCTATATATTG-3') represented by SEQ ID NO: 7 of Sequence Listing using the chromosomal DNA of *Alkaliphillus transvaalensis* as a template. The PCR conditions were that after thermal denaturation at 94° C. for 1 minute, a cycle of 94° C. for 1 minute, 55° C. for 1 minute and 72° C. for 2 minutes was repeated 30 times. The resulting PCR amplification fragment was end-blunted with T4 DNA polymerase (manufactured by Takara Bio), and the end was further phosphorylated with T4 Polynucleotide Kinase (manufactured by Takara Bio). This DNA fragment was bound to vector pHY300PLK (manufactured by Yakult Honsha) digested with Sma I to prepare a recombinant plasmid. *B. subtilis* ISW1214 strain was transformed using this plasmid. The resulting transformant was aerobically shake-cultured in a medium comprising 3% (w/v) polypeptone S, 0.5% fish meat extract, 0.1% yeast extract, 0.1% potassium primary phosphate, 0.02% magnesium sulfate, 3% maltose separately sterilized and tetracycline (15 µg/ml) at 30° C. for 72 hours. As a result, from 0.1 to 2 units (PU), per liter of the culture solution, of alkaline protease ALTP as the invention enzyme was obtained.

The enzymatic activity of the invention enzyme was measured by the following methods.

(a) Casein Method 1 ml of each 50 mmol/L buffer containing 1% (w/v) casein (Hammerstein, Merck) was warmed at 40° C. for 5 minutes, and 0.1 ml of the enzyme solution was then added. A reaction was conducted for from 15 to 20 minutes. Subsequently, 2 ml of a trichloroacetic acid solution (TCA solution: 0.11 mol/L trichloroacetic acid, 0.22 mol/L sodium acetate and 0.33 mol/L acetic acid) was added to terminate the reaction. The reaction solution was allowed to stand at room temperature for 10 minutes, and the acid-modified protein was filtered (No. 2 filter paper, manufactured by Watman). 2.5 ml of an alkaline copper reagent [1% (w/v) potassium sodium tartrate: 1% (w/v) copper sulfate: 2% (w/v) sodium carbonate/0.1 mol/L sodium hydroxide=1:1:100] was added to 0.5 ml of the filtrate, and the mixture was warmed at 30° C. for 10 minutes. Thereafter, 0.25 ml of a dilute phenol reagent [phenol reagent (manufactured by Kanto Kagaku) diluted twofold with deionized water] was added, and the mixture was warmed at 30° C. for 30 minutes. Absorbance at 660 nm was measured with a spectrophotometer to obtain an amount of an acid-soluble protein hydrolyzate. By the way, a system obtained by mixing the enzyme reaction system with a reaction terminator and adding the enzyme solution thereto was used as a blank.

Herein, one unit (PU) of the enzyme referred to an amount of an enzyme in which to liberate the acid-soluble protein hydrolyzate corresponding to 1 µmol of tyrosine for 1 minute under the foregoing reaction conditions.

(b) Synthetic Substrate Method 0.9 ml of 100 mmol/L borate buffer (pH=10.0, containing 2 mmol/L calcium chloride) was mixed with 0.05 ml of a 50 mmol/L synthetic substrate solution (solution obtained by dissolving a p-nitroanilide derivative of an oligopeptide in dimethyl sulfoxide), and the mixture was warmed at 30° C. for 5 minutes. Then, 0.05 ml of the enzyme solution was added, and a reaction was conducted at 30° C. for 10 minutes. 2 ml of a 5% (w/v) citric acid solution was added to terminate the reaction. Absorbance at 420 nm was measured with a spectrophotometer to quantify liberated p-nitroaniline.

Herein, one unit (PU) of the enzyme referred to an amount of an enzyme required to liberate 1 µmol of p-nitroaniline for 1 minute under the foregoing reaction conditions.

(vi) Properties of Alkaline Protease ALTP

The properties of alkaline protease ALTP as the invention enzyme obtained in (v) were as follows.

(a) Optimum pH and pH Stability

The invention enzyme was reacted at 40° C. for 15 minutes in various buffers of pH 3.5 to 12.6 containing 1% (w/v) casein as a substrate, and the enzymatic activity at each pH was measured. The results thereof are shown in FIG. 1A in terms of relative activity when the highest activity was defined as 100%. Alkaline protease ALTP of the invention exhibited the highest activity even at pH 12.6 in 50 mmol/L potassium chloride/sodium hydroxide buffer.

The buffers used and the pH ranges thereof are as follows.

Acetate buffer (□): pH 3.5 to 6.0, phosphate buffer (■): pH 6.5 to 8.1, carbonate buffer (○): pH 9.0 to 11.0, phosphate/sodium hydroxide buffer (●): pH 11.0 to 12.2, and potassium chloride/sodium hydroxide buffer (▲): pH 11.5 to 12.6.

The pH stability of alkaline protease ALTP was measured at pH 3 to 12 using Britton-Robinson wide-ranging buffer. That is, the invention enzyme solution was incorporated into 20 mmol/L Britton-Robinson buffer, and treatment was conducted at 50° C. for 10 minutes. After the treated solution was cooled with ice, the residual activity was measured by the casein method. The results are shown in FIG. 1B in which activity before treatment is defined as 100%. From the results, alkaline protease ALTP of the invention was found to be stable in the pH range of from 5 to 11.

(b) Optimum Temperature 0.1 ml of the invention enzyme solution was added to 1 ml of 50 mmol/L borate buffer (pH 10.0) containing 0.5% (w/v) casein as a substrate, and a reaction was conducted at a temperature of from 30 to 85° C. for 15 minutes. Activity was measured by the casein method. Relative activity at each temperature is shown in FIG. 2A in which activity in the absence of calcium chloride at 50° C. is defined as 100%. "●" indicates relative activity in the absence of calcium chloride, and "○" relative activity in the presence of calcium chloride. Alkaline protease ALTP of the invention was found to have the optimum reaction temperature at 70° C. Further, activity curves in the absence of calcium chloride and in the presence of calcium chloride almost overlapped with each other, and the optimum reaction temperature was found to be little influenced by addition of calcium chloride (5 mmol/L).

(c) Thermostability

The invention enzyme was added to 50 mmol/L borate buffer (pH 10.0), and heat treatment was conducted at each temperature of from 30 to 75° C. for 10 minutes. The residual activity was measured by the casein method. The residual activity after the heat treatment is shown in FIG. 2B in which activity before the heat treatment is defined as 100%. It was found that alkaline protease ALTP of the invention had stable excellent activity up to 65° C. without activity drop by heating. No improvement in thermostability by addition of calcium chloride (5 mmol/L) was observed.

(d) Influence of Metal Ions

The solution of alkaline protease ALTP of the invention was added to 20 mmol/L borate buffer (pH 10.0) containing a metal salt at each concentration as shown in Table 3, and treatment was conducted at 30° C. for 20 minutes. Subsequently, the residual activity was measured by the casein method. The results are shown in Table 3 in terms of a relative value when activity without addition of the metal salt is defined as 100%.

TABLE 3

| Metal salt | Concentration (mmol/L) | Residual activity (%) |
|---|---|---|
| $LiCl_2$ | 1.0 | 114 |
| KCl | 1.0 | 111 |
| NaCl | 1.0 | 112 |
| $BaCl_2$ | 1.0 | 100 |
| $CaCl_2$ | 1.0 | 118 |
| $CdCl_2$ | 1.0 | 100 |
| $CuCl_2$ | 1.0 | 109 |
| $CoCl_2$ | 1.0 | 92 |
| $HgCl_2$ | 1.0 | 15 |
| $MgCl_2$ | 1.0 | 105 |
| $MnCl_2$ | 1.0 | 113 |
| $NiCl_2$ | 1.0 | 94 |
| $FeCl_2$ | 1.0 | 120 |
| $FeCl_3$ | 1.0 | 110 |
| $PbCl_2$ | 1.0 | 115 |
| $SnCl_2$ | 1.0 | 108 |
| $ZnCl_2$ | 1.0 | 121 |
| no addition | — | 100 |

Alkaline protease ALTP of the invention was quite stable to the metal ions. However, it was found to be inhibited by $Hg^{2+}$ (residual activity 15%).

(e) Influence of Surfactants

Influence of surfactants on alkaline protease ALTP of the invention was examined. That is, the invention enzyme solution was added to 0.1 mol/L Tris-hydrochloride buffer (pH 9.0), and each of various surfactants shown in Table 4 was added to the solution. The treatment was conducted at 40° C. for 4 hours. Subsequently, the solution was properly diluted with 50 mmol/L borate buffer (pH 10.5) containing 2 mmol/L calcium chloride, and the residual activity was measured by the casein method. The residual activity was expressed in terms of a relative value when an activity value (treatment time 0 minute) immediately after addition of the enzyme to each sample was defined as 100%. The results are shown in Table 4.

TABLE 4

| Surfactant | Concentration (%) | Residual activity (%) |
|---|---|---|
| Linear sodium alkylbenzene sulfonate*[1] | 1.0 | 98 |
| Sodium polyoxyethylene alkyl sulfate*[2] | 1.0 | 99 |
| Sodium dodecyl sulfate*[3] | 10.0 | 104 |
| Sodium α-olefin sulfonate*[4] | 1.0 | 128 |
| Sodium alkane sulfonate*[5] | 10.0 | 107 |
| α-sulfo-fatty acid ester*[6] | 1.0 | 106 |
| Polyoxyethylene alkyl alcohol*[7] | 1.0 | 107 |

*[1]alkyl: C10 to C14
*[2]alkyl: C9 to C17, POE: 1 to 5 mol
*[3]alkyl: C9 to C17 (C12 - main component)
*[4]alkyl: C7 to C15, $CH_2$: 0.1 to 5 mol
*[5]alkyl (R + R'): C13 to C18
*[6]alkyl (R): C10 to C16, (R'): C1 to C6
*[7]alkyl: C9 to C17, POE: 1 to 5 mol (f) Molecular Weight A molecular weight of alkaline protease ALTP of the invention was measured by sodium dodecyl sulfate (SDS)-polyacrylamide gel electrophoresis. As a molecular weight marker, phosphorylase b (molecular weight: 94,000), bovine serum albumin (molecular weight: 67,000), egg albumin (molecular weight: 43,000), carbonic anhydrase (molecular weight: 30,000), soybean trypsin inhibitor (molecular weight: 20,100) and α-lactoalbumin (molecular weight: 14,400) which are marker kits for a low molecular weight (manufactured by Pharmacia) were used. From FIG. 4, it was estimated that the invention enzyme sample had the molecular weight of from approximately 31,000 to 32,000.

(g) Inhibitor

Each inhibitor was added to 20 mmol/L phosphate buffer (pH 7) at a predetermined concentration, and the invention enzyme was added thereto. The solution was warmed at 30° C. for 20 minutes. Subsequently, the resulting solution was approximately diluted with 50 mmol/L borate buffer (pH 10), and the residual activity was measured. The results are shown in Table 5. It was found that alkaline protease ALTP of the invention was completely inhibited by PMSF and chymostatin as a serine protease inhibitor. However, it was little inhibited even in the presence of EDTA as a chelating agent.

TABLE 5

| Inhibitor | Concentration in treatment | Residual activity (%) |
|---|---|---|
| no addition | — | 100 |
| EDTA | 100 mM | 100 |
| PMSF | 1.0 mM | 0 |
| N-bromosuccinic acid imide | 1.0 mM | 104 |
| Iodine acetate | 1.0 mM | 104 |
| Chymostatin | 30 ppm | 0 |
| Peptain | 1.0 mM | 94 |
| Antipain | 0.1 mM | 94 |
| Leupeptin | 0.1 mM | 100 |
| Bestatin | 0.1 mM | 106 |

EXAMPLE 2

Action of Alkaline Protease ALTP on a Synthetic Substrate

Reactivity of alkaline protease ALTP of the invention with each synthetic substrate was measured using synthetic oligopeptide substrates shown in Table 6.

0.9 ml of 100 mmol/L borate buffer (pH=10.0, containing 2 mmol/L calcium chloride) was mixed with 0.05 ml of a 50 mmol/L synthetic substrate solution shown in Table 6. After the mixture was warmed at 30° C. for 5 minutes, 0.05 ml of the enzyme solution was added thereto, and the reaction was conducted at 30° C. for 10 minutes. 2 ml of a 5% (w/v) citric acid solution was added to terminate the reaction. Absorbance at 420 nm was measured using a spectrophotometer, and p-nitroaniline liberated was quantified.

Activity to N-succinyl-Ala-Ala-Pro-Phe-p-nitroanilide (AAPF (SEQ ID NO: 8)) is the highest, and relative activity to each synthetic substrate is shown in Table 6 in which this activity is defined as 100%.

TABLE 6

| Synthetic substrate | Relative activity (%) |
| --- | --- |
| AAPF (SEQ ID NO: 8) | 100 |
| AAPL (SEQ ID NO: 9) | 91 |
| AAPM (SEQ ID NO: 10) | 74 |
| AIPM (SEQ ID NO: 11) | 90 |
| AAVA (SEQ ID NO: 12) | 4.6 |

Herein, AAPF (SEQ ID NO: 8) is short for N-succinyl-Ala-Ala-Pro-Phe-p-nitroanilide, AAPL (SEQ ID NO: 9) for N-glutaryl-Ala-Ala-Pro-Leu-p-nitroanilide, AAPM (SEQ ID NO: 10) for N-succinyl-Ala-Ala-Pro-Met-p-nitroanilide, AIPM (SEQ ID NO: 11) for N-methoxysuccinyl- Ala-Ile-Pro-Met-p-nitroanilide, and AAVA (SEQ ID NO: 12) for N-succinyl-Ala-Ala-Val-Ala-p- nitroanilide.

It showed activity to, besides the foregoing synthetic substrates, butyroxycarboxy-Leu-Ser- Thr-Arg-p-nitroanilide (LSTR (SEQ ID NO: 13)), N-succinyl-Ala-Ala-Ala-p-nitroanilide (AAA), N-succinyl-Ala-Ala-p-nitroanilide (AA), N-p-tosyl-Gly-Pro-Lys-p-nitroanilide (To-GPK), N- succinyl-Gly-Gly-Phe-p-nitroanilide (GGF), N-carboxybenzoxy-Phe-Val-Arg-p-nitroanilide (Z- FVR) and N-carbobenzoxy-Pro-citrulline-p-nitroanilide (CBZ-Pro-Cit).

EXAMPLE 3

Cleavage of Acidic Insulin B-Chain by Alkaline Protease (ALTP)

(i) Confirmation of Initial Cleavage Sites 3 ng of alkaline protease ALTP was added to a solution obtained by adding 0.1 mg of insulin B-chain to 100 µl of 0.1 mol/L Tris-hydrochloride buffer (pH 8.0), and a reaction was conducted at 30° C. for from 1 to 5 minutes. 5 µl of the solution was collected after 1 minute, 2 minutes and 5 minutes from the start-up of the reaction, and the reaction was terminated by addition of 50 µl of a 2% (v/v) acetonitrile/0.1% trifluoroacetic acid solution (pH 2.2). The reaction solutions were analyzed by liquid chromatograph/tandem mass analyzer (LC/MS/MS). A mixture of fragmental peptides digested with alkaline protease ALTP of the invention was separated and concentrated by capillary HPLC, and ionized to obtain MS and MS/MS spectra. The MS/MS data of the peptides was subjected to Turbo Sequest search to identify the digested acidic insulin B-chain fragments and determine the cleavage sites. Because of the search with the MS/MS data, the highly reliable identification results were obtained.

(ii) Confirmation of all Cleavage Sites

A reaction was conducted at 30° C. for 24 hours under the same conditions as in (i) by changing the concentration of alkaline protease ALTP to 300 ng. After the termination of the reaction, the acidic insulin B-chain fragment digested with alkaline protease ALTP was identified by the foregoing method to determine cleavage sites.

These results are shown in FIG. 3. An arrow indicates a peptide bond in which alkaline protease ALTP cleaves the acidic insulin B-chain, and a thick arrow indicates a cleavage point within 5 minutes at the initial stage. No. 1 shows alkaline protease ALTP of the invention. For comparison, the states of the cleavages of the acidic insulin B-chain by known alkaline proteases found in documents are also shown in FIG. 3. No. 2 shows subtilisin Sendai, No. 3 M-protease, No. 4 subtilisin Carlsberg, and No. 5 subtilisin BPN'.

As is apparent from FIG. 3, it has been found that alkaline protease ALTP of the invention first cleaves Leu-Tyr and when a reaction time is prolonged, cleavage points are increased, and that when alkaline protease ALTP is used in an amount of 300 ng, 26 peptide bonds of 29 peptide bonds except Phe-Val and Thr-Pro-Lys bonds are cleaved within 24 hours. Meanwhile, the various known alkaline proteases do not show many cleavage points, as is clear from FIG. 3. Thus, alkaline protease ALTP of the invention is said to be a novel enzyme having the peculiar activity which is not observed in the ordinary enzymes.

INDUSTRIAL APPLICABILITY

The alkaline protease derived from *Alkaliphillus transvaalensis* in the invention has still excellent activity under quite high alkaline conditions with pH 12 or more and in the presence of various surfactants, and it is useful as a protease which is used by being incorporated into various detergents employed in high alkalinity.

More specifically, it can be utilized in all industries for hydrolysis of proteins in heavy and light detergents, detergents for an automatic flatware washer, cleaners, toilet aromas, bath water purification, piping washing, production of oligopeptides, edible meat softening, leather tanning, allergen removal, digestive agents, environmental purification and the like.

BRIEF DESCRIPTION OF THE DRAWINGS

Figure 3:
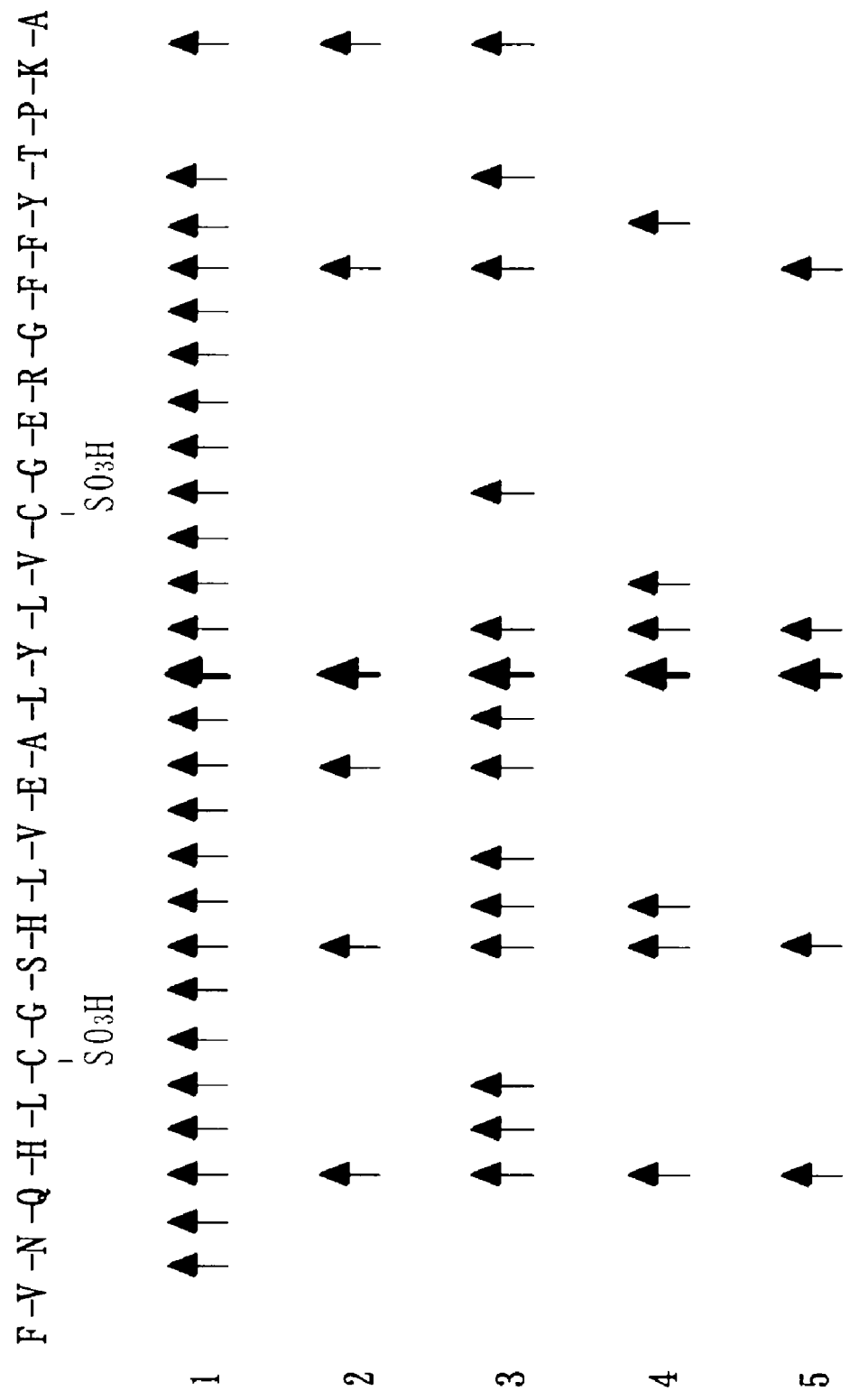

FIG. 3 It is a view showing cleavage of acidic insulin B-chain by the invention enzyme and known alkaline proteases (Figure discloses SEQ ID NO: 17).

SEQUENCE LISTING

<160> NUMBER OF SEQ ID NOS: 17

Figure 1:
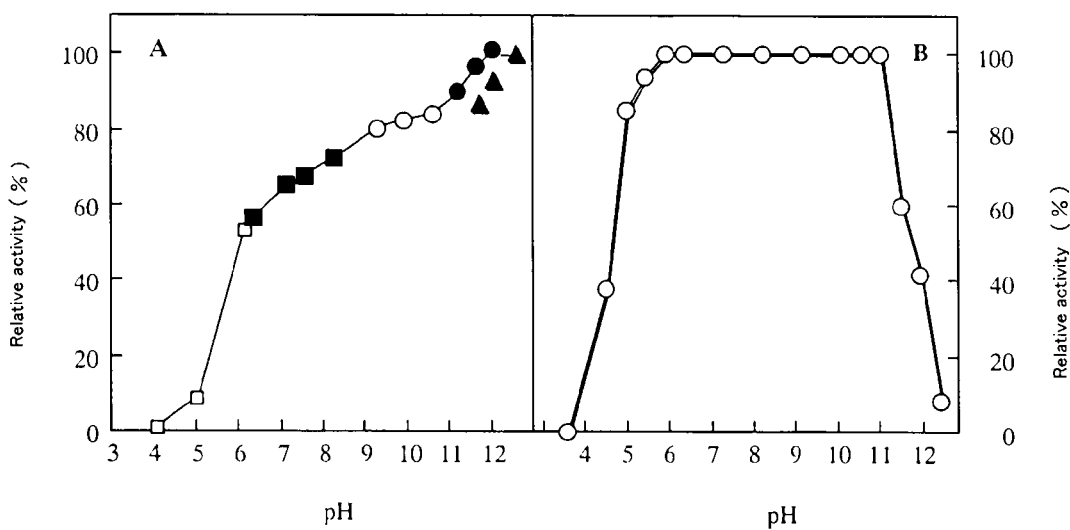
FIG. 1 It is a graph showing a relation of enzymatic activity and pH of the invention enzyme.
Figure 2:
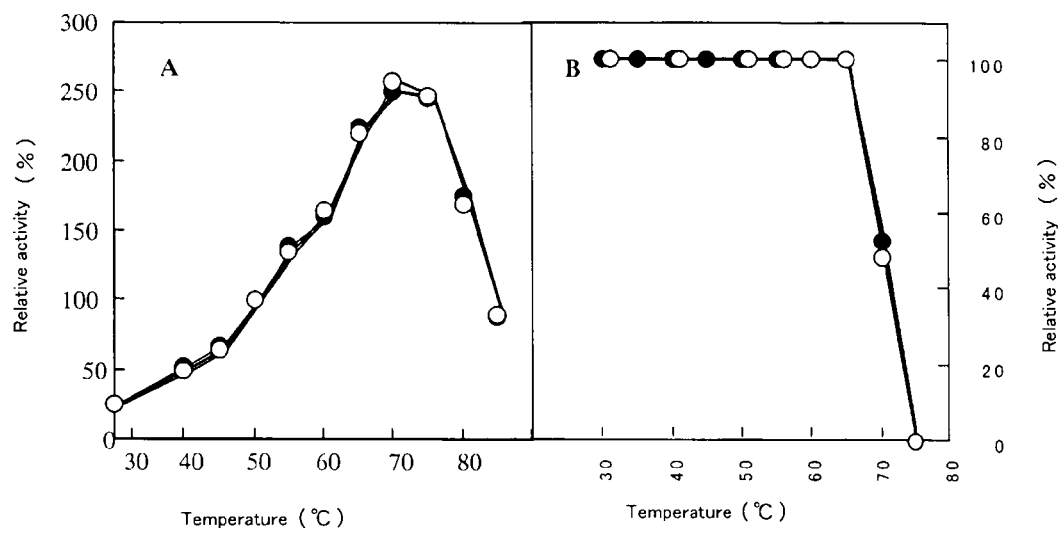
FIG. 2 It is a graph showing a relation of enzymatic activity and a temperature of the invention enzyme.
Figure 4:
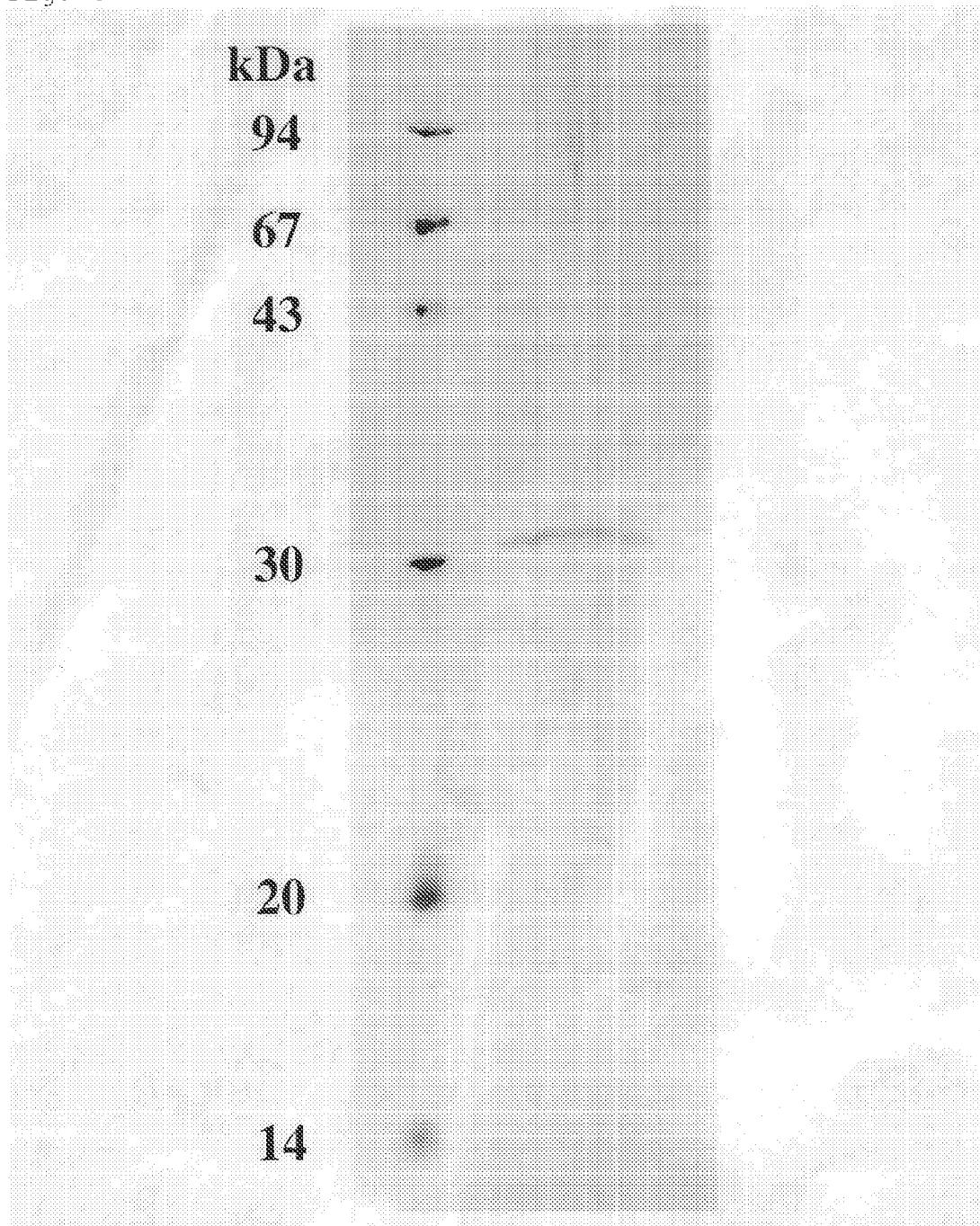
FIG. 4 It is a view showing the results of SDS polyacrylamide gel electrophoresis of the invention enzyme.

<210> SEQ ID NO 1
<211> LENGTH: 1131
<212> TYPE: DNA
<213> ORGANISM: Alkaliphillus transvaalensis
<220> FEATURE:
<221> NAME/KEY: CDS
<222> LOCATION: (1)..(1128)

<400> SEQUENCE: 1

| | | | | | | | | | | | | | | | | |
|---|---|---|---|---|---|---|---|---|---|---|---|---|---|---|---|---|
| atg | aag | aag | atg | ttg | gct | gtt | tta | atg | ata | ctt | gtt | tta | agt | atc | ggg | 48 |
| Met | Lys | Lys | Met | Leu | Ala | Val | Leu | Met | Ile | Leu | Val | Leu | Ser | Ile | Gly | |
| 1 | | | | 5 | | | | | 10 | | | | | 15 | | |
| atc | ttg | gtt | cct | gtt | tct | gca | tcg | gta | tct | gca | gag | aat | gag | aaa | caa | 96 |
| Ile | Leu | Val | Pro | Val | Ser | Ala | Ser | Val | Ser | Ala | Glu | Asn | Glu | Lys | Gln | |
| | | | 20 | | | | | 25 | | | | | 30 | | | |
| gag | tat | ttg | gta | ggg | ttt | aat | ggc | aag | gca | agc | aga | ggc | cta | gtt | caa | 144 |
| Glu | Tyr | Leu | Val | Gly | Phe | Asn | Gly | Lys | Ala | Ser | Arg | Gly | Leu | Val | Gln | |
| | | 35 | | | | | 40 | | | | | 45 | | | | |
| gct | ttt | ggt | gtt | cag | aat | gag | gca | att | ctt | cac | gag | ttc | caa | tat | att | 192 |
| Ala | Phe | Gly | Val | Gln | Asn | Glu | Ala | Ile | Leu | His | Glu | Phe | Gln | Tyr | Ile | |
| 50 | | | | | 55 | | | | | 60 | | | | | | |
| gat | aca | gta | tta | atg | gag | tta | act | cct | gct | caa | gct | aag | gct | tta | gct | 240 |
| Asp | Thr | Val | Leu | Met | Glu | Leu | Thr | Pro | Ala | Gln | Ala | Lys | Ala | Leu | Ala | |
| 65 | | | | | 70 | | | | | 75 | | | | | 80 | |
| aat | aac | cct | aat | gtt | gaa | tac | gtt | gaa | gaa | aac | gca | gaa | gtt | cat | ctt | 288 |
| Asn | Asn | Pro | Asn | Val | Glu | Tyr | Val | Glu | Glu | Asn | Ala | Glu | Val | His | Leu | |
| | | | | 85 | | | | | 90 | | | | | 95 | | |
| tta | gca | caa | agt | act | cct | tgg | gga | gta | act | cgt | gta | caa | gct | cct | aac | 336 |
| Leu | Ala | Gln | Ser | Thr | Pro | Trp | Gly | Val | Thr | Arg | Val | Gln | Ala | Pro | Asn | |
| | | | 100 | | | | | 105 | | | | | 110 | | | |
| gta | tgg | aac | aga | gga | ttt | aca | ggt | tct | ggc | gtt | aga | gtt | gct | gta | tta | 384 |
| Val | Trp | Asn | Arg | Gly | Phe | Thr | Gly | Ser | Gly | Val | Arg | Val | Ala | Val | Leu | |
| | | 115 | | | | | 120 | | | | | 125 | | | | |
| gat | act | ggt | att | cat | tct | tcc | cat | gaa | gat | tta | aca | gta | tct | ggt | gga | 432 |
| Asp | Thr | Gly | Ile | His | Ser | Ser | His | Glu | Asp | Leu | Thr | Val | Ser | Gly | Gly | |
| | 130 | | | | | 135 | | | | | 140 | | | | | |
| tac | tct | gtg | ttt | gga | gac | tct | cct | tac | aat | gat | gta | caa | gga | cat | gga | 480 |
| Tyr | Ser | Val | Phe | Gly | Asp | Ser | Pro | Tyr | Asn | Asp | Val | Gln | Gly | His | Gly | |
| 145 | | | | | 150 | | | | | 155 | | | | | 160 | |
| act | cat | gtt | gct | ggt | aca | att | gct | gct | aga | aac | aat | tct | gtt | gga | gta | 528 |
| Thr | His | Val | Ala | Gly | Thr | Ile | Ala | Ala | Arg | Asn | Asn | Ser | Val | Gly | Val | |
| | | | | 165 | | | | | 170 | | | | | 175 | | |
| att | ggt | gtt | gct | tac | aac | gct | caa | tta | tac | gca | gta | aaa | gtt | tta | aat | 576 |
| Ile | Gly | Val | Ala | Tyr | Asn | Ala | Gln | Leu | Tyr | Ala | Val | Lys | Val | Leu | Asn | |
| | | | 180 | | | | | 185 | | | | | 190 | | | |
| aac | caa | ggt | agt | ggt | aca | ctt | gct | ggt | atc | gct | caa | ggt | atc | gag | tgg | 624 |
| Asn | Gln | Gly | Ser | Gly | Thr | Leu | Ala | Gly | Ile | Ala | Gln | Gly | Ile | Glu | Trp | |
| | | 195 | | | | | 200 | | | | | 205 | | | | |
| gca | aga | caa | aac | aac | atg | cat | gtt | att | aac | atg | agt | tta | ggt | gga | act | 672 |
| Ala | Arg | Gln | Asn | Asn | Met | His | Val | Ile | Asn | Met | Ser | Leu | Gly | Gly | Thr | |
| | 210 | | | | | 215 | | | | | 220 | | | | | |
| agt | ggt | tct | aca | act | tta | caa | aac | gca | gtt | aac | gct | gct | tat | aat | gca | 720 |
| Ser | Gly | Ser | Thr | Thr | Leu | Gln | Asn | Ala | Val | Asn | Ala | Ala | Tyr | Asn | Ala | |
| 225 | | | | | 230 | | | | | 235 | | | | | 240 | |
| ggt | att | tta | gta | gtt | gct | gct | gct | ggt | aac | agt | gga | aat | tct | gct | gga | 768 |
| Gly | Ile | Leu | Val | Val | Ala | Ala | Ala | Gly | Asn | Ser | Gly | Asn | Ser | Ala | Gly | |
| | | | | 245 | | | | | 250 | | | | | 255 | | |
| aca | ggc | gac | aac | gtt | ggt | ttc | cca | gct | aga | tat | cca | aat | gca | atg | gca | 816 |

```
Thr Gly Asp Asn Val Gly Phe Pro Ala Arg Tyr Pro Asn Ala Met Ala
            260                 265                 270 gtt gct gca aca act tct gga aac gtt aga gca tct ttc tct agt act      864
Val Ala Ala Thr Thr Ser Gly Asn Val Arg Ala Ser Phe Ser Ser Thr
            275                 280                 285 ggt cca gct gta gaa atc gca gct cct gga caa gat atc aat agt act      912
Gly Pro Ala Val Glu Ile Ala Ala Pro Gly Gln Asp Ile Asn Ser Thr
            290                 295                 300 tat cca act aat act tat aga tca tta aat ggt act tct atg gca gct      960
Tyr Pro Thr Asn Thr Tyr Arg Ser Leu Asn Gly Thr Ser Met Ala Ala
305                 310                 315                 320 cct cat gtt gct ggt gtt gca gct tta tta aag tct gca aga cct gct     1008
Pro His Val Ala Gly Val Ala Ala Leu Leu Lys Ser Ala Arg Pro Ala
            325                 330                 335 gta aca gct gca gga att aga aat gct atg aac agt act gca ctt aac     1056
Val Thr Ala Ala Gly Ile Arg Asn Ala Met Asn Ser Thr Ala Leu Asn
            340                 345                 350 tta gga aac tct aac tgg tac gga aat gga cta gta aga gca aac aat     1104
Leu Gly Asn Ser Asn Trp Tyr Gly Asn Gly Leu Val Arg Ala Asn Asn
            355                 360                 365 gca ctt gat atg gta tta agc tac taa                                 1131
Ala Leu Asp Met Val Leu Ser Tyr
            370                 375

<210> SEQ ID NO 2
<211> LENGTH: 376
<212> TYPE: PRT
<213> ORGANISM: Alkaliphillus transvaalensis

<400> SEQUENCE: 2

Met Lys Lys Met Leu Ala Val Leu Met Ile Leu Val Leu Ser Ile Gly
1               5                   10                  15

Ile Leu Val Pro Val Ser Ala Ser Val Ser Ala Glu Asn Glu Lys Gln
            20                  25                  30

Glu Tyr Leu Val Gly Phe Asn Gly Lys Ala Ser Arg Gly Leu Val Gln
        35                  40                  45

Ala Phe Gly Val Gln Asn Glu Ala Ile Leu His Glu Phe Gln Tyr Ile
    50                  55                  60

Asp Thr Val Leu Met Glu Leu Thr Pro Ala Gln Ala Lys Ala Leu Ala
65                  70                  75                  80

Asn Asn Pro Asn Val Glu Tyr Val Glu Glu Asn Ala Glu Val His Leu
                85                  90                  95

Leu Ala Gln Ser Thr Pro Trp Gly Val Thr Arg Val Gln Ala Pro Asn
            100                 105                 110

Val Trp Asn Arg Gly Phe Thr Gly Ser Gly Val Arg Val Ala Val Leu
        115                 120                 125

Asp Thr Gly Ile His Ser Ser His Glu Asp Leu Thr Val Ser Gly Gly
    130                 135                 140

Tyr Ser Val Phe Gly Asp Ser Pro Tyr Asn Asp Val Gln Gly His Gly
145                 150                 155                 160

Thr His Val Ala Gly Thr Ile Ala Ala Arg Asn Asn Ser Val Gly Val
                165                 170                 175

Ile Gly Val Ala Tyr Asn Ala Gln Leu Tyr Ala Val Lys Val Leu Asn
            180                 185                 190

Asn Gln Gly Ser Gly Thr Leu Ala Gly Ile Ala Gln Gly Ile Glu Trp
        195                 200                 205

Ala Arg Gln Asn Asn Met His Val Ile Asn Met Ser Leu Gly Gly Thr
    210                 215                 220
```

```
Ser Gly Ser Thr Thr Leu Gln Asn Ala Val Asn Ala Ala Tyr Asn Ala
225                 230                 235                 240

Gly Ile Leu Val Val Ala Ala Ala Gly Asn Ser Gly Asn Ser Ala Gly
                245                 250                 255

Thr Gly Asp Asn Val Gly Phe Pro Ala Arg Tyr Pro Asn Ala Met Ala
            260                 265                 270

Val Ala Ala Thr Thr Ser Gly Asn Val Arg Ala Ser Phe Ser Ser Thr
        275                 280                 285

Gly Pro Ala Val Glu Ile Ala Ala Pro Gly Gln Asp Ile Asn Ser Thr
    290                 295                 300

Tyr Pro Thr Asn Thr Tyr Arg Ser Leu Asn Gly Thr Ser Met Ala Ala
305                 310                 315                 320

Pro His Val Ala Gly Val Ala Ala Leu Leu Lys Ser Ala Arg Pro Ala
                325                 330                 335

Val Thr Ala Ala Gly Ile Arg Asn Ala Met Asn Ser Thr Ala Leu Asn
            340                 345                 350

Leu Gly Asn Ser Asn Trp Tyr Gly Asn Gly Leu Val Arg Ala Asn Asn
        355                 360                 365

Ala Leu Asp Met Val Leu Ser Tyr
    370                 375

<210> SEQ ID NO 3
<211> LENGTH: 279
<212> TYPE: PRT
<213> ORGANISM: Alkaliphillus transvaalensis

<400> SEQUENCE: 3

Ala Gln Ser Thr Pro Trp Gly Val Thr Arg Val Gln Ala Pro Asn Val
1               5                   10                  15

Trp Asn Arg Gly Phe Thr Gly Ser Gly Val Arg Val Ala Val Leu Asp
                20                  25                  30

Thr Gly Ile His Ser Ser His Glu Asp Leu Thr Val Ser Gly Gly Tyr
            35                  40                  45

Ser Val Phe Gly Asp Ser Pro Tyr Asn Asp Val Gln Gly His Gly Thr
        50                  55                  60

His Val Ala Gly Thr Ile Ala Ala Arg Asn Asn Ser Val Gly Val Ile
65                  70                  75                  80

Gly Val Ala Tyr Asn Ala Gln Leu Tyr Ala Val Lys Val Leu Asn Asn
                85                  90                  95

Gln Gly Ser Gly Thr Leu Ala Gly Ile Ala Gln Gly Ile Glu Trp Ala
            100                 105                 110

Arg Gln Asn Asn Met His Val Ile Asn Met Ser Leu Gly Gly Thr Ser
        115                 120                 125

Gly Ser Thr Thr Leu Gln Asn Ala Val Asn Ala Ala Tyr Asn Ala Gly
    130                 135                 140

Ile Leu Val Val Ala Ala Ala Gly Asn Ser Gly Asn Ser Ala Gly Thr
145                 150                 155                 160

Gly Asp Asn Val Gly Phe Pro Ala Arg Tyr Pro Asn Ala Met Ala Val
                165                 170                 175

Ala Ala Thr Thr Ser Gly Asn Val Arg Ala Ser Phe Ser Ser Thr Gly
            180                 185                 190

Pro Ala Val Glu Ile Ala Ala Pro Gly Gln Asp Ile Asn Ser Thr Tyr
        195                 200                 205

Pro Thr Asn Thr Tyr Arg Ser Leu Asn Gly Thr Ser Met Ala Ala Pro
    210                 215                 220
```

```
His Val Ala Gly Val Ala Ala Leu Leu Lys Ser Ala Arg Pro Ala Val
225                 230                 235                 240

Thr Ala Ala Gly Ile Arg Asn Ala Met Asn Ser Thr Ala Leu Asn Leu
            245                 250                 255

Gly Asn Ser Asn Trp Tyr Gly Asn Gly Leu Val Arg Ala Asn Asn Ala
        260                 265                 270

Leu Asp Met Val Leu Ser Tyr
        275

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 4
gcncarwsna cnccntgggg                                            20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 5
ccngcnacrt gngtnccrtg                                            20

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6 cattttaca ccaatattta cattttaatt ccaag                              35

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atttccagct atttatctcc ttctatatat tg                                32

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Pro Phe
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Pro Leu
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ala Pro Met
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ile Pro Met
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 12

Ala Ala Val Ala
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Ser Thr Arg
1

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gln Ser Thr Pro Trp Gly Val Thr Arg
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Ala Ala Pro His Val Ala Gly Val
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly His Gly Thr His Val Ala Gly
1               5

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

The invention claimed is:

1. An isolated or purified alkaline protease
that comprises the amino acid sequence of SEQ ID NO: 3 or an amino acid sequence that results from the deletion, substitution, situs inversus arrangement, insertion, or addition of one to ten amino acids of SEQ ID NO: 3; or
that comprises an amino acid sequence having at least 75% homology to SEQ ID NO: 3.

2. The isolated or purified alkaline protease of claim 1 that comprises the amino acid sequence of SEQ ID NO: 3 or an amino acid sequence that results from the deletion, substitution, situs inversus arrangement, insertion, or addition of one to ten amino acids of SEQ ID NO: 3.

3. The isolated or purified alkaline protease of claim 1 that comprises an amino acid sequence that results from the insertion or addition of one to ten amino acids to SEQ ID NO: 3.

4. The isolated or purified alkaline protease of claim 1 that comprises an amino acid sequence that results from the deletion of one to ten amino acids of SEQ ID NO: 3.

5. The isolated or purified alkaline protease of claim 1 that comprises an amino acid sequence that results from the substitution of one to ten amino acids of SEQ ID NO: 3.

6. The isolated or purified alkaline protease of claim 1 that comprises an amino acid sequence having at least 75% homology to SEQ ID NO: 3.

7. The isolated or purified alkaline protease of claim 1 that comprises an amino acid sequence having at least 96% homology to SEQ ID NO: 3.

8. The isolated or purified alkaline protease of claim 1 that comprises SEQ ID NO: 3.

9. A method for digesting a polypeptide comprising contacting said polypeptide with the isolated or purified alkaline protease of claim 1.

10. The method of claim 9, wherein said polypeptide is contacted with said alkaline protease in the presence of a surfactant.

11. The method of claim 9, wherein said polypeptide is contacted with said alkaline protease in the presence of at least one surfactant selected from the group consisting of linear sodium alkylbenzene sulfonate, sodium polyoxyethylene alkyl sulfate, sodium dodecyl sulfate, sodium α-olefin sulfonate, sodium alkane sulfonate, α-sulfo-fatty acid ester and polyoxyethylene alkyl alcohol.

12. The method of claim 9, wherein said polypeptide is contacted with said alkaline protease in the presence of calcium ions.

13. The method of claim 9, wherein said polypeptide is contacted with said alkaline protease at a pH ranging from 5 to 13.

14. The method of claim 9, wherein said polypeptide is contacted with said alkaline protease at a temperature ranging from 30° C. to 85° C.

15. The method of claim 9, wherein said polypeptide is contacted with said alkaline protease at a temperature of about 70° C.

16. The method of claim 9, wherein said polypeptide is an insulin-B chain, casein, elastin, keratin, or hemoglobin.

17. The method of claim 9, wherein said polypeptide is N-succinyl-Ala-Ala-Pro-Phe-p-nitroanilide ("Ala-Ala-Pro-Phe" disclosed as SEQ ID NO: 8), N-glutaryl-Ala-Ala-Pro-Leu-p-nitroanilide ("Ala-Ala-Pro-Leu" disclosed as SEQ ID NO: 9), N-succinyl-Ala-Ala-Pro-Met-p-nitroanilide ("Ala-Ala-Pro-Met" disclosed as SEQ ID NO: 10), N-methoxysuccinyl-Ala-Ile-Pro-Met-p-nitroanilide ("Ala-Ile-Pro-Met" disclosed as SEQ ID NO: 11) or N-succinyl-Ala-Ala-Val-Ala-p-nitroanilide ("Ala-Ala-Val-Ala" disclosed as SEQ ID NO: 12).

18. An isolated or purified polynucleotide that encodes the alkaline protease of claim 1.

19. A recombinant vector comprising the polynucleotide according to claim 18.

20. A microorganism which is transformed with the recombinant vector according to claim 19.

21. A process for producing an isolated or purified alkaline protease comprising culturing the microorganism of claim 20 and recovering the alkaline protease.

22. An isolated or purified alkaline protease precursor
that comprises the amino acid sequence of SEQ ID NO: 2 or an amino acid sequence that results from the deletion, substitution, situs inversus arrangement, insertion, or addition of one to ten amino acids of SEQ ID NO: 2; or
that comprises an amino acid sequence having at least 75% homology to SEQ ID NO: 2.

23. The isolated or purified alkaline protease precursor of claim 22 that comprises the amino acid sequence of SEQ ID NO: 2 or an amino acid sequence that results from the deletion, substitution, situs inversus arrangement, insertion, or addition of one to ten amino acids of SEQ ID NO: 2.

24. The isolated or purified alkaline protease precursor of claim 22 that comprises an amino acid sequence that results from the insertion or addition of one to ten amino acids to SEQ ID NO: 2.

25. The isolated or purified alkaline protease precursor of claim 22 that comprises an amino acid sequence that results from the deletion of one to ten amino acids of SEQ ID NO: 2.

26. The isolated or purified alkaline protease precursor of claim 22 that comprises an amino acid sequence that results from the substitution of one to ten amino acids of SEQ ID NO: 2.

27. The isolated or purified alkaline protease precursor of claim 22 that comprises an amino acid sequence having at least 75% homology to SEQ ID NO: 2.

28. The isolated or purified alkaline protease precursor of claim 22 that comprises an amino acid sequence having at least 96% homology to SEQ ID NO: 2.

29. The isolated or purified alkaline protease precursor of claim 22 that comprises SEQ ID NO: 2.

30. A method for digesting a polypeptide comprising contacting said polypeptide with the isolated or purified alkaline protease precursor of claim 22 or a fragment thereof that has alkaline protease activity.

31. An isolated or purified polynucleotide that encodes the alkaline protease precursor of claim 22.

32. A recombinant vector comprising the polynucleotide according to claim 31.

33. A microorganism which is transformed with the recombinant vector according to claim 32.

34. A process for producing an isolated or purified alkaline protease precursor comprising culturing the microorganism of claim 33 and recovering the alkaline protease precursor.

* * * * *